United States Patent

Lindsay et al.

[11] Patent Number: 5,958,338
[45] Date of Patent: Sep. 28, 1999

[54] MOUNTING APPARATUS FOR BLOOD HANDLING SYSTEMS

[75] Inventors: Erin J. Lindsay, Manchester; Ronald J. Leonard, Ann Arbor, both of Mich.

[73] Assignee: Terumo Cardiovascular Systems Corporation, Somerset, N.J.

[21] Appl. No.: 08/962,360

[22] Filed: Oct. 31, 1997

[51] Int. Cl.⁶ .......................... A61M 1/14; A61M 37/00; F16D 31/00; B64D 47/00
[52] U.S. Cl. .................................. 422/45; 600/19; 604/4; 60/325
[58] Field of Search ................................. 600/19; 422/45; 261/DIG. 28; 604/4; 333/202; 60/325

[56] References Cited

U.S. PATENT DOCUMENTS

| | | |
|---|---|---|
| 614,888 | 11/1898 | Poetz . |
| 617,591 | 1/1899 | Miller et al. . |
| 978,029 | 12/1910 | Kell . |
| 981,866 | 1/1911 | Lockhart . |
| 1,592,093 | 7/1926 | Foucault . |
| 1,871,421 | 8/1932 | Muhlhauser et al. . |
| 1,885,321 | 11/1932 | Benn . |
| 2,279,733 | 4/1942 | Cross ...................................... 285/143 |
| 2,362,856 | 11/1944 | Strunk et al. ........................... 287/104 |
| 2,870,863 | 1/1959 | Bramhall .................................. 183/43 |
| 3,694,793 | 9/1972 | Concelman ............................... 339/91 |
| 3,891,416 | 6/1975 | Leonard et al. .......................... 55/178 |
| 3,949,553 | 4/1976 | Schneider ................................. 60/325 |
| 3,993,461 | 11/1976 | Leonard et al. .......................... 55/178 |
| 4,011,532 | 3/1977 | Williams et al. ......................... 333/98 |
| 4,014,329 | 3/1977 | Welch et al. ............................. 128/214 |
| 4,188,785 | 2/1980 | Ando et al. ............................... 60/325 |
| 4,208,193 | 6/1980 | Munsch et al. ............................ 55/36 |
| 4,243,531 | 1/1981 | Crockett et al. ......................... 210/188 |
| 4,305,180 | 12/1981 | Schwartz ................................... 24/221 |
| 4,424,190 | 1/1984 | Mather et al. ............................ 422/46 |
| 4,432,766 | 2/1984 | Bellotti et al. .......................... 604/283 |
| 4,655,762 | 4/1987 | Rogers ..................................... 604/403 |
| 4,705,497 | 11/1987 | Shitaokoshi et al. ...................... 604/4 |
| 4,708,370 | 11/1987 | Todd ........................................ 285/12 |
| 4,826,477 | 5/1989 | Adams ......................................... 604/4 |
| 4,904,001 | 2/1990 | Sasa et al. ................................ 285/316 |
| 4,941,517 | 7/1990 | Galloway .................................... 141/1 |
| 4,944,883 | 7/1990 | Schoendorfer et al. ................. 210/782 |
| 5,039,430 | 8/1991 | Corey ....................................... 210/806 |

(List continued on next page.)

FOREIGN PATENT DOCUMENTS

| | | |
|---|---|---|
| 0705616 | 4/1996 | European Pat. Off. . |
| 2261933 | 7/1974 | Germany . |
| WO 89/05666 | 6/1989 | WIPO . |
| WO 90/01970 | 8/1990 | WIPO . |
| 93/25249 | 12/1993 | WIPO . |
| 97/33672 | 9/1997 | WIPO . |

OTHER PUBLICATIONS

Article: Sarns Membrane Oxygenator; Compendium of in vitro, ex vivo, and in vivo Performance Characteristics, 1987.
Sarns/3M SMO/IR Training Manual, Jan. 13, 1989.

*Primary Examiner*—Ronald Stright
*Assistant Examiner*—Cheryl L. Huseman
*Attorney, Agent, or Firm*—Burns, Doane, Swecker & Mathis, LLP

[57] ABSTRACT

A blood handling system has a first blood handling apparatus mounted on a second blood handling apparatus with a mounting apparatus. The mounting apparatus has two primary components: a retention sleeve attached to a stem that protrudes from the lower portion of the first blood handling apparatus; and a slotted plate that is attached to a stem on the second blood handling apparatus. The retention sleeve has a track for receiving the slotted plate and a flexible tab, with a protruding tooth, that securely engages the slotted plate in a locked position. If it becomes necessary to disconnect the first blood handling apparatus from the second blood handling apparatus during surgery, the tab may be easily moved into an unlocked position, allowing the disk to slide freely out of the track so that the units can be easily separated from each other.

33 Claims, 5 Drawing Sheets

U.S. PATENT DOCUMENTS

| | | | |
|---|---|---|---|
| 5,149,318 | 9/1992 | Lindsay | 604/4 |
| 5,150,788 | 9/1992 | Weissman | 206/369 |
| 5,270,005 | 12/1993 | Raible | 422/46 |
| 5,304,164 | 4/1994 | Lindsay | 604/403 |
| 5,586,791 | 12/1996 | Kirchner et al. | 285/179 |
| 5,649,903 | 7/1997 | Deniega et al. | 604/4 |
| 5,658,023 | 8/1997 | Mercer et al. | 285/184 |
| 5,700,041 | 12/1997 | Andre et al. | 285/325 |
| 5,747,138 | 5/1998 | Leonard | 428/113 |
| 5,762,868 | 6/1998 | Leonard | 422/46 |
| 5,824,212 | 10/1998 | Brockhoff | 210/194 |
| 5,849,186 | 12/1998 | Raneri et al. | 210/315 |

& # x20;

MOUNTING APPARATUS FOR BLOOD HANDLING SYSTEMS

FIELD OF THE INVENTION

This invention relates to blood handling systems used in surgery, such as blood oxygenators and reservoirs, and to devices for joining together two blood handling apparatuses in an extracorporeal circuit. In particular, the invention relates to an apparatus for mounting a blood reservoir on a blood oxygenator.

BACKGROUND

During cardiovascular surgery a patient's heart is temporarily unable to properly oxygenate and circulate blood unaided. Extracorporeal circuits have therefore been developed to provide necessary circulation support. Typically, a venous line drains blood from the right side of the patient's heart and delivers it to a blood reservoir. Blood is then pumped, by a specially designed blood pump, from the outlet of the blood reservoir into a blood oxygenator, for oxygenation and cooling. The oxygenated blood is then delivered via an arterial line to the patient. While the pump is running, the patient returns blood to the venous line to repeat the cycle.

The support circuit normally also includes a blood scavenging sub-circuit for recovering blood from the surgical field to recycle the blood. The scavenging sub-circuit includes one or more suckers (typically two to four) for sucking blood from the surgical field. Vacuum is applied to the suckers by a peristaltic positive displacement pump (also known as a roller pump) or wall vacuum to deliver the scavenged blood to a cardiotomy reservoir. A cardiotomy reservoir includes a defoaming section, because the scavenged blood normally includes a large amount of entrained air, and a filter for filtering the scavenged blood. The outlet for the cardiotomy reservoir delivers the de-foamed, filtered blood to the venous blood reservoir of the main circuit. U.S. Pat. Nos. 3,891,416; 3,993,461; 4,208,193; and 4,243,531 show various cardiotomy reservoirs.

The cardiotomy reservoir may alternatively be an integral portion of the venous blood reservoir, in which the scavenged blood flows through a filter section and the venous blood does not. Both the scavenged blood and venous blood would flow through a defoaming section.

Of course, there are numerous permutations of the basic circuit and sub-circuit, in addition to those described above, that have been employed to provide circulatory support.

Although extracorporeal circuits effectively sustain vital circulatory functions during surgery, it is not uncommon for one of the elements of the system to wear out or fail during a surgical procedure. Most notably, blood oxygenators and reservoirs contain filters and fibrous material that may become damaged or clogged and require replacement. When this occurs the flow of blood in the circuit must be momentarily stopped and the defective elements quickly removed and replaced.

Both time and ease of use are of the essence in making such a change. To facilitate efficient management of the extracorporeal system, especially when an element has failed, it would be advantageous to have a system that is compact and that has elements that may be releasably mounted to each other or to support structures. An apparatus for mounting blood handling devices, such as blood reservoirs and oxygenators, to each other or to support structures would also make it possible to construct extracorporeal circuits that are vertically compressed and flatter. These systems would not only economize on space in the operating room, but would also provide better venous drainage.

U.S. Pat. No. 5,304,164 discloses a bayonet-style mounting apparatus that releasably attaches an oxygenator to a reservoir with pins retained in L-shaped slots.

SUMMARY OF THE INVENTION

The invention provides an apparatus for mounting one blood handling apparatus on another blood handling apparatus that is simpler to use and allows for the construction of more compact units. The mounting apparatus comprises a slotted plate portion and a retention sleeve portion for releasably engaging the slotted plate portion. The retention sleeve portion is adapted to attach to a first blood handling apparatus by means of a stem, and the slotted plate is adapted to attach to a second blood handling apparatus by means of a second stem. The retention sleeve has a horizontal base with a flange projecting perpendicular to the base. The flange has two parallel sides that form a track for retaining the slotted plate and an opening to receive the slotted plate. The base has a flexible tab with a tooth for releasably engaging and retaining the slotted plate. The flexible tab is adapted to be moved between at least a first unlocked position and a second locked position. The slotted plate is adapted to both rotate and slide freely in and out of the track, when the tab is in the unlocked position. In the locked position, the flexible tab firmly engages the slotted plate with a tooth. In one embodiment of the invention the flexible tab is adapted to be moved to a third semi-locked position in which the slotted plate may be rotated in the track but cannot slide in the track.

The invention also provides a blood handling apparatus that is adapted to be releasably mounted on a second blood handling apparatus in an extracorporeal circuit using the mounting apparatus of the invention. The blood handling apparatus comprises a housing, a stem attached to the housing, and a retention sleeve attached to the stem for releasably engaging a slotted plate on another blood handling apparatus. In an alternative embodiment, the blood handling apparatus has a slotted plate instead of a retention sleeve mounted on a stem.

The invention further provides a blood handling system that includes a first blood handling apparatus that is releasably mounted on a second blood handling apparatus by means of a mounting apparatus. The mounting apparatus includes a slotted plate portion and a retention sleeve portion adapted to releasably engage the slotted plate portion. The retention sleeve portion is attached to the first blood handling apparatus by means of a stem, and the slotted plate portion is attached to the second blood handling apparatus by means of a second stem. The retention sleeve has a base with a flange projecting perpendicular to the base. The flange has two parallel sides that form a track for retaining the slotted plate. The flange has an opening to receive the slotted plate. The base includes a flexible tab with a tooth for releasably engaging the slotted plate. The flexible tab is adapted to move between at least a first unlocked position and a second locked position. In the unlocked position, the slotted plate rotates and slides freely within the track. In the locked position, the flexible tab firmly engages the slotted plate.

The invention also includes an embodiment wherein the flexible tab further comprises a ramped structure that abuts the tooth and projects farther from the tab than the tooth. The tab is adapted to be moved to a third semi-locked position in which the slotted plate may be rotated in the track but cannot slide in the track.

The invention further provides embodiments of the blood handling system in which a blood reservoir is mounted on a blood oxygenator using the mounting apparatus of the invention.

In addition the invention provides a blood handling system having a blood handling apparatus mounted to a support structure with the mounting apparatus of the invention. A retention sleeve is attached to either the support structure or the blood handling apparatus, and a slotted plate is attached to the other apparatus.

BRIEF DESCRIPTION OF THE FIGURES

The invention will be further described with reference to the drawings, wherein corresponding reference characters indicate corresponding parts throughout the several views, and wherein.

DETAILED DESCRIPTION OF PREFERRED EMBODIMENTS

The present invention provides an apparatus for releasably mounting one blood handling apparatus on another blood handling apparatus or a support structure, in an extracorporeal circuit used during surgical procedures. The releasable mounting apparatus of the invention allows a blood reservoir and oxygenator to be slidingly coupled, and then uncoupled by moving a single flexible tab from one position to another.

Figure 1:
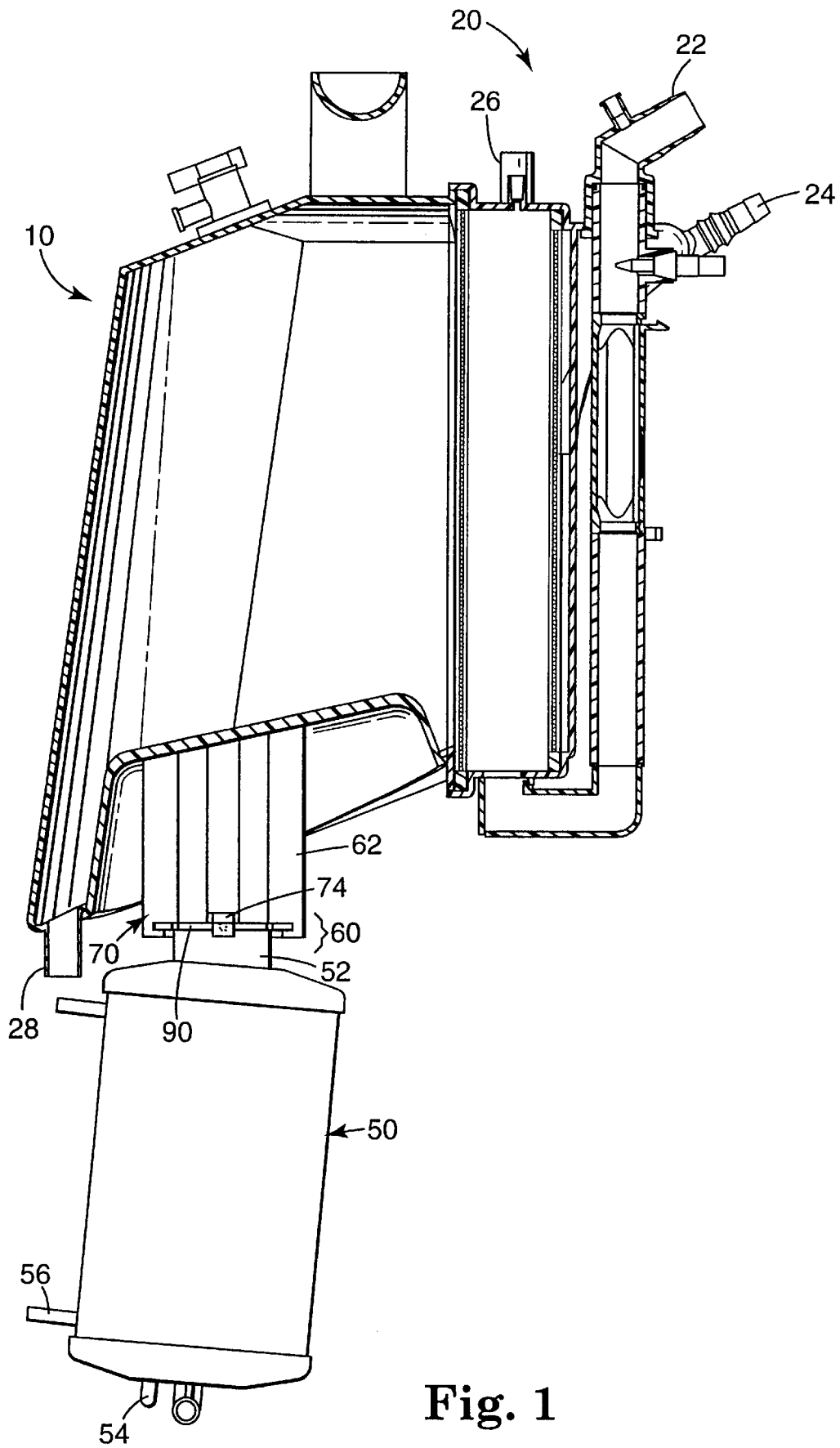
FIG. 1 is a side view of a preferred embodiment of the blood handling system of the present invention.
Figure 2:
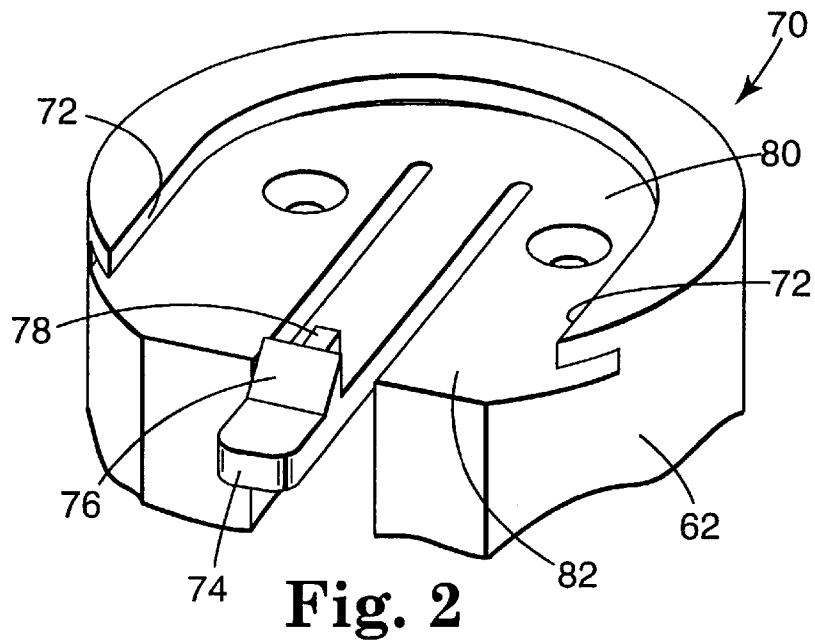
FIG. 2 is a perspective view of a retention sleeve of a preferred embodiment of the mounting apparatus of the invention.
Figure 3:
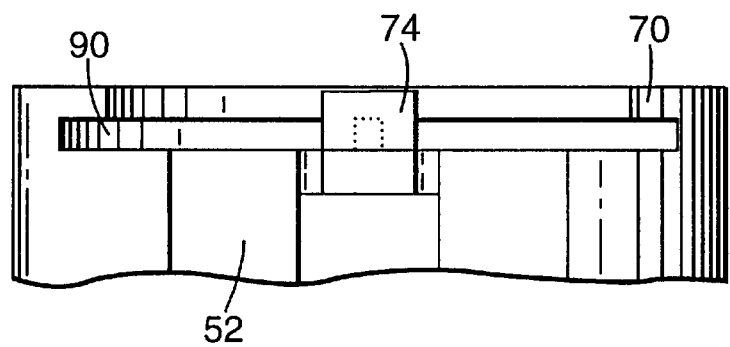
FIG. 3 is a side view of a preferred embodiment of the mounting apparatus of the invention.

The invention includes a blood handling system 10, best shown in FIG. 1, in which a first blood handling apparatus 20 is mounted on a second blood handling apparatus 50 with mounting apparatus 60. In a preferred embodiment of the invention, the blood handling apparatuses 20 and 50 may be any apparatuses commonly employed in an extracorporeal circuit. In a more preferred embodiment of the invention, blood handling apparatus 20 is a blood reservoir and blood handling apparatus 50 is a blood oxygenator. In the most preferred embodiment of the blood handling system of the invention, shown in FIG. 1, blood handling apparatus 20 is a blood reservoir of the type described in U.S. patent application Ser. No. 08/565,438, filed Jun. 7, 1997, which is incorporated in its entirety herein by reference; and blood apparatus 50 is an oxygenator of the type described in U.S. patent application Ser. No. 08/565,438, filed Nov. 30, 1995; U.S. patent application Ser. No. 08/565,439, filed Nov. 30, 1995; and 08/822,523, filed Apr. 16, 1997, which are incorporated herein by reference. Venous blood enters blood reservoir 20 through venous inlet 22, cardiotomy sucker port 24 and auxiliary cardiotomy inlet 26. Defoamed and filtered blood exits blood reservoir 20 through outlet 28 and is pumped to oxygenator 50. The blood enters oxygenator 50 through inlet 54 and after oxygenation is returned to the patient through outlet 56.

As shown in FIG. 1, mounting apparatus 60 includes a slotted plate 90 and a retention sleeve 70 that is adapted to releasably engage slotted plate 90. Slotted plate 90 is attached to blood oxygenator 50 by oxygenator stem 52. Retention sleeve 70 is attached to blood reservoir 20 by reservoir stem 62.

In a preferred embodiment of the invention, oxygenator 50 is tilted at an oblique angle to assist in priming of the oxygenator, and oxygenator stem 52 is canted so that slotted plate 90 and retention sleeve 70 are horizontal when mounted. In a more preferred embodiment of the invention the oxygenator is inclined between about 2 degrees and about 30 degrees and in the most preferred embodiment the oxygenator is inclined about 8 degrees. Preferably both oxygenator stem 52 and reservoir stem 62 are oriented generally vertically.

Figure 4:
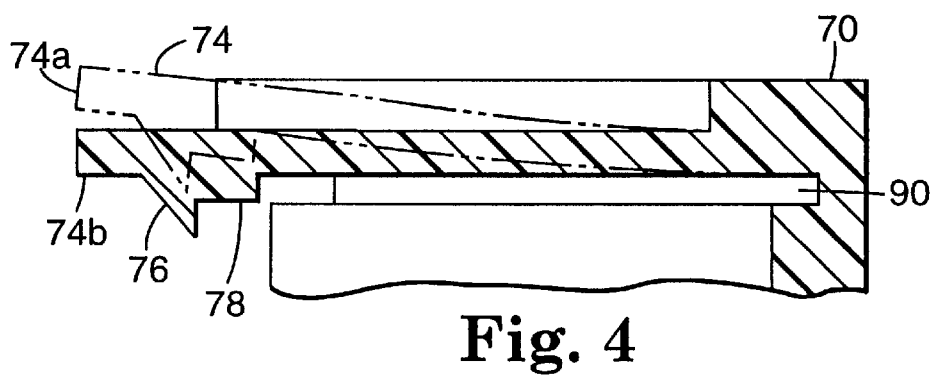
FIG. 4 is a side view of a retention sleeve of a preferred embodiment of the mounting apparatus of the invention, showing the locked and unlocked positions of the flexible tab.
Figure 5:
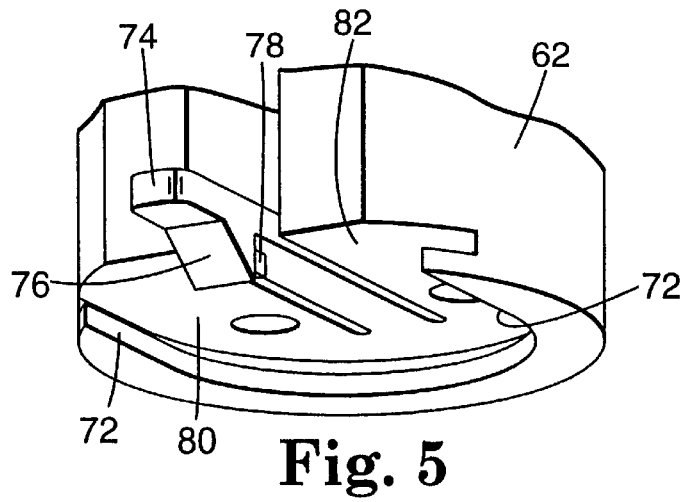
FIG. 5 is a perspective view of a retention sleeve of the preferred embodiment of the blood handling system of the invention, showing the sleeve attached to a blood reservoir stem.

Retention sleeve 70 of the mounting apparatus 60 is shown in FIGS. 2–5 and 7. Retention sleeve 70 includes a horizontally oriented base 80 with a flange 72 that projects in a direction perpendicular to the base 80. The flange 72 has two parallel sides that form a track for retaining slotted plate 90. An opening 82 in the flange 72 allows the slotted plate 90 to be inserted in the track for mounting. As shown in FIG. 4, the base 80 of the retention sleeve 70 includes a flexible tab 74 that may be moved between an unlocked position 74*a* and a locked position 74*b*, but which is resiliently biased to its locked position. In the unlocked position 74*a*, a tooth 78 on the flexible tab 74 is biased away from the track formed by flange 72, and slotted plate 90 may be inserted or removed from the track and rotated freely. In the locked position 74*b*, best shown in FIGS. 3 and 7, slotted plate 90 is inserted in retention sleeve 70, and tooth 78 of flexible tab 74 firmly engages one of the slots 92, thus preventing the slotted plate 90 from either rotating or sliding in the track.

In the most preferred embodiment of the invention, flexible tab 74 also includes a ramped structure 76 that abuts tooth 78 and projects farther from tab 74 than tooth 78. In this embodiment, flexible tab 74 may be moved to a third, semi-locked position in which slotted plate 90 may be rotated freely within retention sleeve 70 but may not slide in the track. In the semi-locked position tooth 78 is disengaged from slot 92, allowing free rotation of slotted disk 90, but ramped structure 78 remains in the path of flange opening 82 and prevents the slotted disk 90 from sliding.

In an alternative embodiment of the invention, not shown, flexible tab 74 includes ramped structure 76 but does not include tooth 78, and plate 90 has a smooth surface and does not include slots. Flexible tab 74 is moved into unlocked position 74a, and plate 90 is inserted into retention sleeve 70. Flexible tab 74 is then moved into the locked position, flush against the perimeter of the plate 90, and prevents plate 90 from sliding along the track but allows rotational movement.

Figure 6:
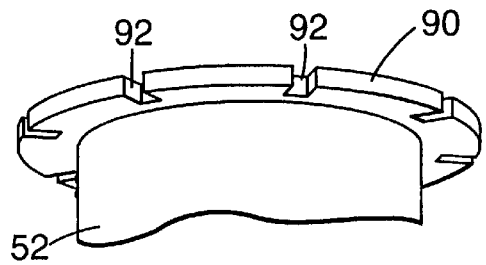
FIG. 6 is a perspective view of the slotted disk of a preferred embodiment of the mounting apparatus of the invention, showing the slotted disk attached to the blood oxygenator stem.
Figure 7:
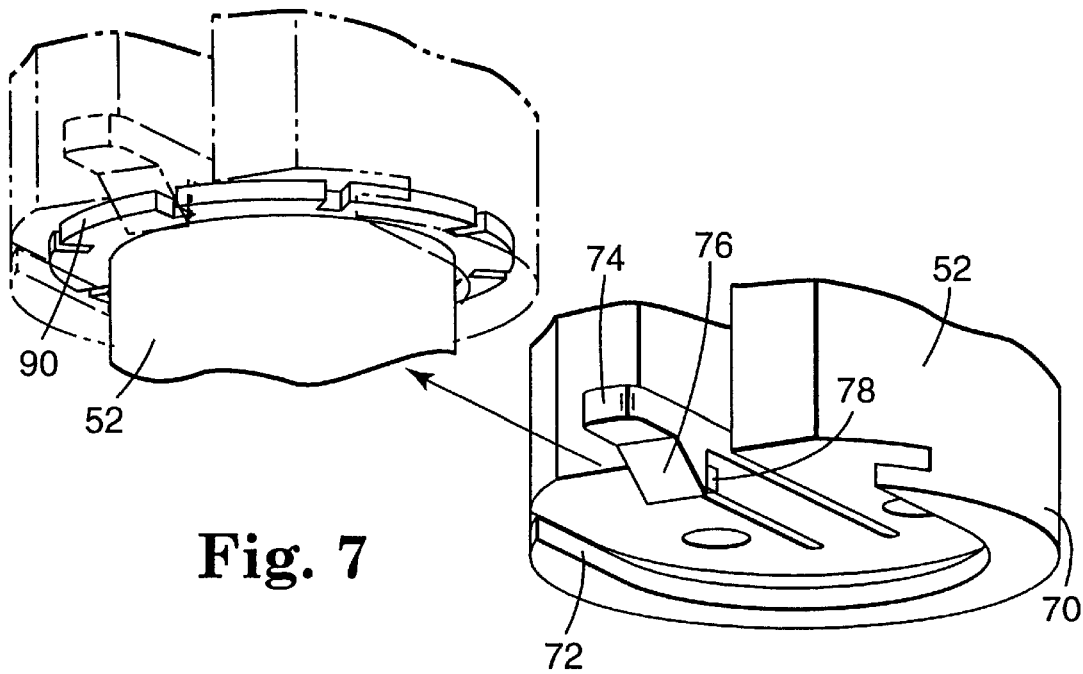
FIG. 7 is a perspective view of a preferred embodiment of the mounting apparatus of the invention, showing the retention sleeve and slotted disk in their mounted and unmounted configurations.
Figure 8:
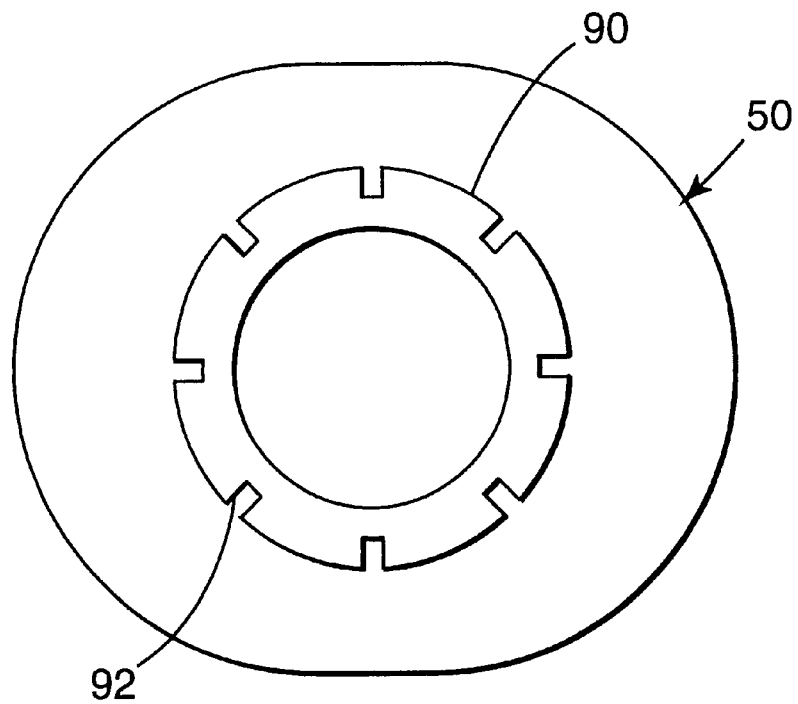
FIG. 8 is a top view of a slotted plate of a preferred embodiment of the mounting apparatus of the invention, attached to a blood oxygenator.
Figure 9:
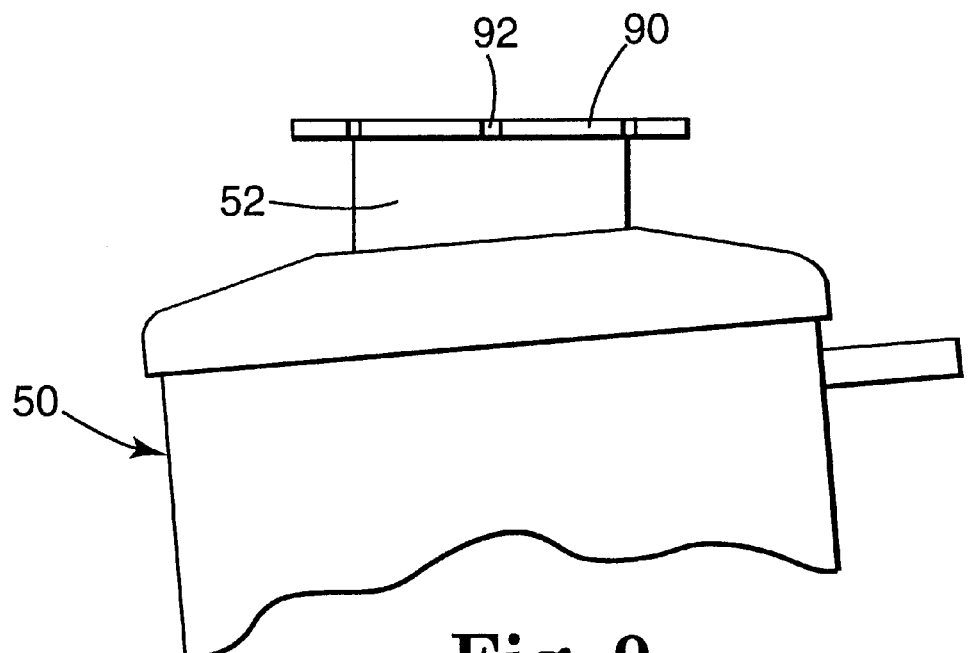
FIG. 9 is a side view of a slotted plate of a preferred embodiment of the mounting apparatus of the invention, attached to a blood oxygenator.

Slotted plate 90 is best shown in FIGS. 6, 8 and 9. Slotted plate 90 includes several slots spaced along its circumference to be engaged by retention sleeve 70. Slotted plate 90 may preferably be any shape that may be engaged in the retention sleeve of the invention, including circular or, for example, a polygon having 3, 4, 5, 6 or more sides. In the most preferred embodiment of the invention, the plate is circular in shape.

Retention sleeve 70 may preferably be made out of any material with sufficient strength, resilience and flexibility to releasably engage and disengage slotted plate 90 through several cycles, including plastics such as polycarbonate or polypropylene, ceramics, aluminum or other metals. In the most preferred embodiment, retention sleeve 70 is made of polycarbonate. Slotted plate 90 may be made out of any material with sufficient strength to support the weight of a blood handling apparatus, including the materials that are suitable for construction of retention sleeve 70. However, the material of slotted plate 90 need not have the resilience and flexibility of retention sleeve 70. In the most preferred embodiment, slotted plate 90 may be made of polycarbonate.

In addition to the blood handling system 10, the invention also includes the various subparts of the blood handling system 10 described above, including the mounting apparatus 60 used to mount blood handling apparatus 20 on blood handling apparatus 50.

The invention also includes a blood handling apparatus that is adapted to be releasably mounted on another blood handling apparatus in an extracorporeal circuit, shown in FIG. 8. Blood oxygenator 50 has a stem 52 with a slotted disk 90 attached to it. The slotted disk 90 is adapted to be engaged by the flexible tab 74 of the retention sleeve 80. In one alternative embodiment, the blood handling apparatus is a blood reservoir. In another alternative embodiment, the blood oxygenator 50 or other blood handling apparatus has a retention sleeve 70 instead of a slotted plate attached to the stem.

Figure 10:
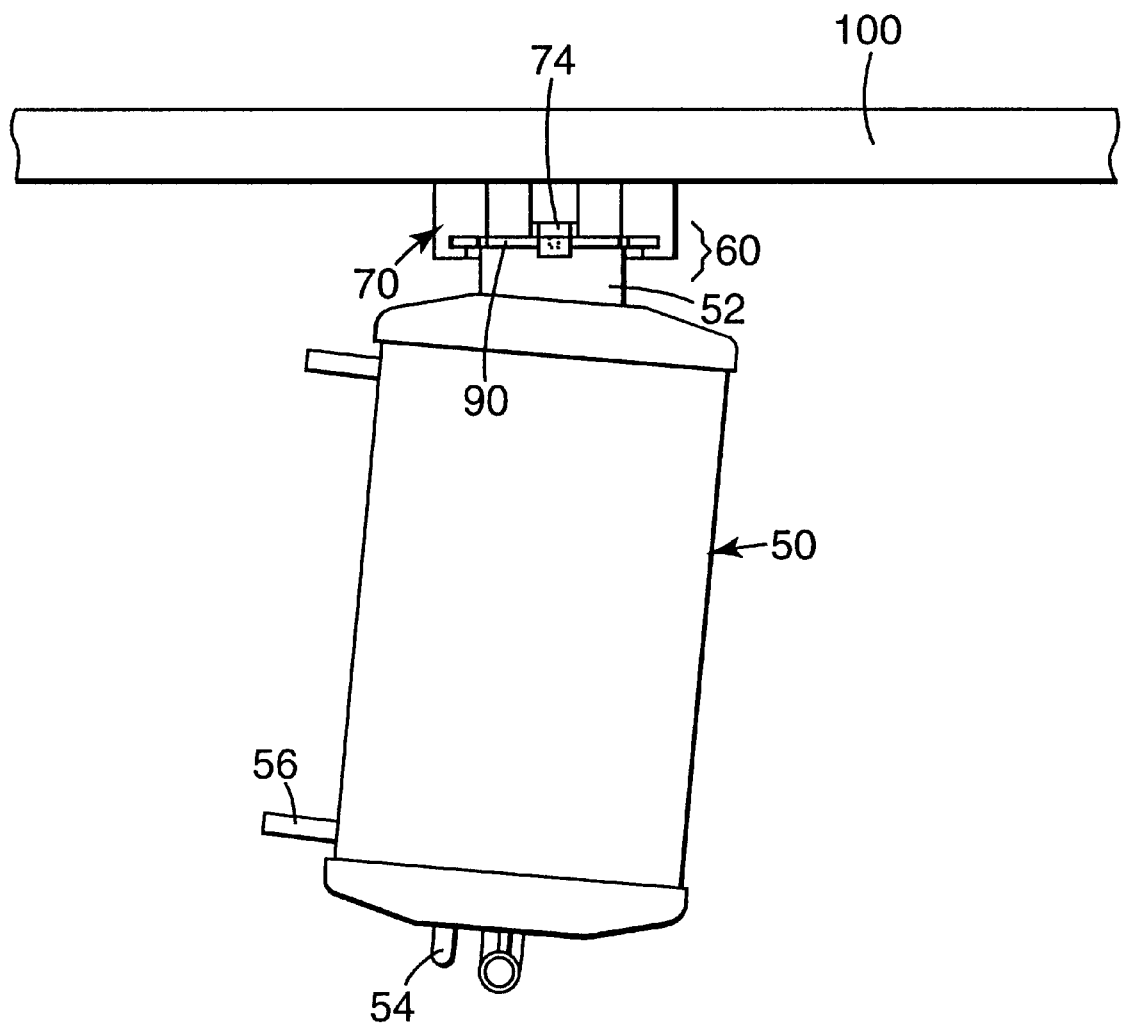
FIG. 10 is a perspective view of a preferred embodiment of a blood handling system according to the invention.

FIG. 10 illustrates an embodiment of the invention in which a blood handling system includes a blood handling apparatus that is mounted on a support structure 100 rather than another blood handling apparatus. Blood reservoir 50 is mounted on support structure 100 with mounting apparatus 60. As shown in FIG. 10, a retention sleeve 70 is attached to support structure 100 for receiving and retaining slotted plate 90 on a blood handling apparatus to be mounted. The blood handling apparatus may be any blood handling apparatus used in an extracorporeal circuit. In the most preferred embodiment, the blood handling apparatus is either a blood reservoir or a blood oxygenator. In a preferred embodiment, either a slotted plate 90 or a retention sleeve 70 may be attached to the support structure to receive a mated member on a blood handling apparatus. In the most preferred embodiment, a retention sleeve 70 is attached to the support structure 100, and a slotted plate 90 is attached to the blood handling apparatus.

Operation

During a surgical procedure the mounting apparatus 60 of the invention may be used to quickly and easily attach and detach two blood handling apparatuses, allowing rapid substitution of worn-out units.

Blood reservoir 20 may be mounted on blood oxygenator 50 by grasping oxygenator 50 with one hand and guiding slotted plate 90, attached to oxygenator 50, into the track formed by flange 72 on retention sleeve 70. When slotted plate 90 contacts ramped structure 76 on retention sleeve 70, flexible tab 74 is deflected upward and out of the path of slotted plate 90 as it advances in the track, and slotted plate 90 slides all the way into retention sleeve 70. After slotted plate 90 is firmly seated in retention sleeve 70, flexible tab 74, no longer deflected by slotted plate 90, moves into locked position 74b in which tooth 78 engages one of the slots 92 in slotted plate 90 and prevents both rotation and sliding of slotted plate 92 in the retention sleeve 70.

To rotate the mounted units relative to each other after they have been mounted, flexible tab 74 is moved upward by hand into a semi-locked position in which tooth 78 is disengaged from slot 92 but ramped structure 76 abuts slotted plate 90 and prevents it from sliding out of the track. Slotted plate 90 may then be rotated freely in retention sleeve 70.

To detach the oxygenator 50 from the reservoir 20, flexible tab 74 is moved upward to unlocked position 74a, and slotted plate 90 is slid out of retention sleeve 70.

What is claimed is:

1. A blood handling system comprising:
   a first blood handling apparatus, a second blood handling apparatus, and a mounting apparatus, with the first blood handling apparatus being adapted to be releasably mounted on the second blood handling apparatus by means of the mounting apparatus;
   the mounting apparatus having a slotted plate and a retention sleeve to releasably engage the slotted plate, the retention sleeve being attached to the first blood handling apparatus, and the slotted plate being attached to the second blood handling apparatus;
   the retention sleeve having a base with a flange projecting from the base, the flange having two parallel sides to form a track for retaining the slotted plate and an opening to receive the slotted plate, the base having a resiliently flexible tab with a tooth for releasably engaging and retaining the slotted plate, the tab being adapted to be moved between at least an unlocked position in which the slotted plate is adapted to both rotate and slide freely in and out of the track, and a locked position in which the flexible tab is resiliently biased to firmly engage the slotted plate with the tooth; and
   the slotted plate having spaced slots along its circumference adapted to be engaged by the tooth on the flexible tab when the tab is in its locked position.

2. A blood handling system according to claim 1, wherein the flexible tab further comprises a ramped structure abutting the tooth and projecting farther from the tab than the tooth, the tab being adapted to be moved to a semi-locked position intermediate the locked and unlocked positions in which the slotted plate may be rotated in the track but cannot slide in the track.

3. A blood handling system according to claim 1, wherein the first blood handling apparatus is one of a blood reservoir and a blood oxygenator, and the second blood handling apparatus is the other of a blood reservoir and a blood oxygenator.

4. A blood handling system according to claim 1, further comprising a first stem attaching the retention sleeve to the first blood handling apparatus, and a second stem attaching the slotted plate to the second blood handling apparatus, the first and second stems being adapted to be generally vertically oriented in use of the system, and the base of the retention sleeve being adapted to be generally horizontally oriented in use of the system.

5. A blood handling system comprising:

a blood reservoir, a blood oxygenator, and a mounting apparatus, with the blood reservoir being adapted to be releasably mounted on the oxygenator by means of the mounting apparatus;

the mounting apparatus having a slotted plate and a retention sleeve for releasably engaging the slotted plate, the retention sleeve being attached to the blood reservoir, and the slotted plate being attached to the blood oxygenator;

the retention sleeve having a base with a flange projecting from the base, the flange having two parallel sides to form a track for retaining the slotted plate and an opening to receive the slotted plate, the base having a resiliently flexible tab with a tooth for releasably engaging and retaining the slotted plate, the tab being adapted to be moved between at least an unlocked position in which the slotted plate is adapted to both rotate and slide freely in and out of the track, and a locked position in which the flexible tab is resiliently biased to firmly engage the slotted plate with the tooth; and the slotted plate having spaced slots along its circumference adapted to be engaged by the tooth on the flexible tab when the tab is in its locked position.

6. A blood handling system according to claim 5, wherein the flexible tab further comprises a ramped structure abutting the tooth and projecting farther from the tab than the tooth, the tab being adapted to be moved to a third semi-locked position in which the slotted plate may be rotated in the track but cannot slide in the track.

7. A blood handling system according to claim 5, wherein the blood oxygenator is inclined at an oblique angle, and the stem attached to the blood oxygenator is canted so that when the blood reservoir is mounted on the blood oxygenator the mounting apparatus is oriented generally horizontally.

8. A blood handling system according to claim 5, wherein the oblique angle is between about 2 degrees and about 30 degrees.

9. A blood handling system according to claim 5, further comprising a first stem attaching the retention sleeve to the blood reservoir, and a second stem attaching the slotted plate to the blood oxygenator, the first and second stems being adapted to be generally vertically oriented in the use of the system, and the base of the retention sleeve being adapted to be generally horizontally oriented in the use of the system.

10. A blood handling system comprising:

a blood reservoir, a blood oxygenator, and a mounting apparatus, with the blood reservoir being adapted to be releasably mounted on the oxygenator by means of the mounting apparatus;

the mounting apparatus having a slotted plate and a retention sleeve for releasably engaging the slotted plate, the retention sleeve being attached to the blood oxygenator, and the slotted plate being attached to the blood reservoir;

the retention sleeve having a base with a flange projecting from the base, the flange having two parallel sides to form a track for retaining the slotted plate and an opening to receive the slotted plate, the base having a resiliently flexible tab with a tooth for releasably engaging and retaining the slotted plate, the tab being adapted to be moved between at least an unlocked position in which the slotted plate is adapted to both rotate and slide freely in and out of the track, and a locked position in which the flexible tab is resiliently biased to firmly engage the slotted plate with the tooth;

the slotted plate having spaced slots along its circumference adapted to be engaged by the tooth on the flexible tab when the tab is in its locked position.

11. A blood handling system according to claim 10, wherein the flexible tab further comprises a ramped structure abutting the tooth and projecting farther from the tab than the tooth, the tab being adapted to be moved to a third semi-locked position in which the slotted plate may be rotated in the track but cannot slide in the track.

12. A blood handling system according to claim 10, wherein the blood oxygenator is inclined at an oblique angle, and the stem attached to the blood oxygenator is canted so that when the blood reservoir is mounted on the blood oxygenator the mounting apparatus is oriented generally horizontally.

13. A blood handling system according to claim 10, wherein the oblique angle is between about 2 degrees and about 30 degrees.

14. A blood handling system according to claim 10, further comprising a first stem attaching the retention sleeve to the blood oxygenator, and a second stem attaching the slotted plate to the blood reservoir, the first and second stems being adapted to be generally vertically oriented in the use of the system, and the base of the retention sleeve being adapted to be generally horizontally oriented in the use of the system.

15. An apparatus for mounting one blood handling apparatus on another blood handling apparatus, the mounting apparatus comprising:

a slotted plate and a retention sleeve for releasably engaging the slotted plate, the retention sleeve being adapted to attach to a first blood handling apparatus by means of a generally vertically oriented first stem, and the slotted plate being adapted to attach to the second blood handling apparatus by means of a generally vertically oriented second stem;

the retention sleeve having a horizontally oriented base with a flange projecting perpendicular to the base, the flange having two parallel sides to form a track for retaining the slotted plate and an opening to receive the slotted plate, the base having a flexible tab with a tooth for releasably engaging and retaining the slotted plate, the flexible tab being adapted to be moved between at least a first unlocked position and a second locked position, the slotted plate being adapted to both rotate and slide freely in and out of the track when the tab is biased in the unlocked position, and the flexible tab being adapted to firmly engage the slotted plate with the tooth when the tab is in the unbiased locked position; and the slotted plate having spaced slots along its circumference adapted to be engaged by the tooth on the flexible tab.

16. A blood handling system according to claim 15, wherein the flexible tab further comprises a ramped structure abutting the tooth and projecting farther from the tab than the tooth, the tab being adapted to be moved to a third semi-locked position in which the slotted plate may be rotated in the track but cannot slide in the track.

17. An apparatus for mounting one blood handling apparatus on another blood handling apparatus according to claim 15, wherein the first blood handling apparatus is a blood reservoir or a blood oxygenator and the second blood handling apparatus is a blood reservoir or a blood oxygenator.

18. A blood handling apparatus adapted to be releasably mounted on another blood handling apparatus in an extracorporeal circuit, the releasably mountable blood handling apparatus comprising:

a housing, a stem attached to the housing, and a retention sleeve attached to the stem for releasably engaging a slotted plate on another blood handling apparatus;

the retention sleeve having a horizontally oriented base with a flange projecting perpendicular to the base, the flange having two parallel sides to form a track for retaining the slotted plate and an opening to receive the slotted plate, the base having a flexible tab with a tooth for releasably engaging and retaining the slotted plate, the flexible tab being adapted to be moved between at least a first unlocked position and a second locked position, the slotted plate being adapted to slide freely in and out of the track when the tab is biased in the unlocked position, and the flexible tab being adapted to firmly engage the slotted plate with the tooth when the tab is biased in the unbiased locked position.

19. A blood handling system according to claim 18, wherein the flexible tab further comprises a ramped structure abutting the tooth and projecting farther from the tab than the tooth, the tab being adapted to be moved to a third semi-locked position in which the slotted plate may be rotated in the track but cannot slide in the track.

20. A releasably mountable blood handling apparatus according to claim 18, wherein the blood handling apparatus is a blood reservoir or a blood oxygenator.

21. A blood handling apparatus adapted to be releasably mounted on another blood handling apparatus in an extracorporeal circuit, the releasably mountable blood handling apparatus comprising:

a housing, a stem attached to the housing, and a slotted plate attached to the stem adapted to be releasably engaged by a retention sleeve on another blood handling apparatus;

the slotted plate having spaced slots along its circumference adapted to be releasably engaged by the tooth on the flexible tab of the retention sleeve, the retention sleeve having a horizontally oriented base with a flange extending perpendicular to the base, the flange having two parallel sides to form a track for retaining the slotted plate and an opening to receive the slotted plate, the base having a flexible tab with a tooth for releasably engaging and retaining the slotted plate, the flexible tab being adapted to be moved between at least a first unlocked position and a second locked position, the slotted plate being adapted to slide freely in and out of the track when the tab is biased in the unlocked position, and the flexible tab being adapted to firmly engage the slotted plate with the tooth when the tab is in the unbiased locked position.

22. A blood handling system according to claim 21, wherein the flexible tab further comprises a ramped structure abutting the tooth and projecting farther from the tab than the tooth, the tab being adapted to be moved to a third semi-locked position in which the slotted plate may be rotated in the track but cannot slide in the track.

23. A releasably mountable blood handling apparatus according to claim 21, wherein the blood handling apparatus is a blood reservoir or a blood oxygenator.

24. A blood handling system comprising:

a first blood handling apparatus, a second blood handling apparatus, and a mounting apparatus, with the first blood handling apparatus being adapted to be releasably mounted on the second blood handling apparatus by means of the mounting apparatus;

the mounting apparatus having a plate and a retention sleeve to releasably engage the plate, the retention sleeve being attached to the first blood handling apparatus by means of a generally vertically oriented first stem, and the plate being attached to the second blood handling apparatus by means of a generally vertically oriented second stem;

the retention sleeve having a horizontally oriented base with a flange projecting perpendicular to the base, the flange having two parallel sides to form a track for retaining the plate and an opening to receive the plate, the base having a flexible tab with a ramped structure for releasably retaining the plate, the flexible tab being adapted to be moved between at least a first unlocked position and a second locked position, the plate being adapted to both rotate and slide freely in and out of the track when the tab is biased in the unlocked position, and the flexible tab being adapted to prevent sliding of the plate with the ramped structure but allow rotational movement when the tab is in an unbiased locked position.

25. A blood handling system according to claim 24, wherein the first blood handling apparatus is a blood reservoir or a blood oxygenator and the second blood handling apparatus is a blood reservoir or a blood oxygenator.

26. A blood handling system comprising:

a blood handling apparatus, a support structure, and a mounting apparatus, with the first blood handling apparatus being adapted to be releasably mounted on the support structure by means of the mounting apparatus;

the mounting apparatus having a slotted plate and a retention sleeve to releasably engage the slotted plate, the retention sleeve being attached to the support structure, and the slotted plate being attached to the blood handling apparatus;

the retention sleeve having a base with a flange projecting from the base, the flange having two parallel sides to form a track for retaining the slotted plate and an opening to receive the slotted plate, the base having a resiliently flexible tab with a tooth for releasably engaging and retaining the slotted plate, the flexible tab being adapted to be moved between at least an unlocked position in which the slotted plate is adopted to both rotate and slide freely in and out of the track, and a second locked position in which the flexible tab is resiliently biased to firmly engage the slotted plate with the tooth; and the slotted plate having spaced slots along its circumference adapted to be engaged by the tooth on the flexible tab when the tab is in its locked position.

27. A blood handling system according to claim 26, wherein the flexible tab further comprises a ramped structure abutting the tooth and projecting farther from the tab than the tooth, the tab being adapted to be moved to a third semi-locked position in which the slotted plate may be rotated in the track but cannot slide in the track.

28. A blood handling system according to claim 26, wherein the blood handling apparatus is a blood reservoir or a blood oxygenator.

29. A blood handling system according to claim 26, further comprising a first stem attaching the retention sleeve to the support structure, and a second stem attaching the slotted plate to the blood handling apparatus, the first and second stems being adapted to be generally vertically oriented in the use of the system, and the base of the retention sleeve being adapted to be generally horizontally oriented in the use of the system.

30. A blood handling system comprising:

a blood handling apparatus, a support structure, and a mounting apparatus, with the blood handling apparatus being adapted to be releasably mounted on the support structure by means of the mounting apparatus;

the mounting apparatus having a slotted plate and a retention sleeve to releasably engage the slotted plate, the retention sleeve being attached to the blood handling apparatus, and the slotted plate being attached to the support structure;

the retention sleeve having a base with a flange projecting from the base, the flange having two parallel sides to form a track for retaining the slotted plate and an opening to receive the slotted plate, the base having a resiliently flexible tab with a tooth for releasably engaging and retaining the slotted plate, the tab being adapted to be moved between at least an unlocked position in which the slotted plate is adapted to both rotate and slide freely in and out of the track, and a locked position in which the flexible tab is resiliently biased to firmly engage the slotted plate with the tooth; and the slotted plate having spaced slots along its circumference adapted to be engaged by the tooth on the flexible tab when the tab is in its locked position.

31. A blood handling system according to claim 30, wherein the flexible tab further comprises a ramped structure abutting the tooth and projecting farther from the tab than the tooth, the tab being adapted to be moved to a third semi-locked position in which the slotted plate may be rotated in the track but cannot slide in the track.

32. A blood handling system according to claim 30, wherein the blood handling apparatus is a blood reservoir or a blood oxygenator.

33. A blood handling system according to claim 30, further comprising a first stem attaching the retention sleeve to the blood handling apparatus, and a second stem attaching the slotted plate to the support structure, the first and second stems being adapted to be generally vertically oriented in the use of the system, and the base of the retention sleeve being adapted to be generally horizontally oriented in the use of the system.

* * * * *